US00PP17411P2

(12) United States Plant Patent
Dirr

(10) Patent No.: US PP17,411 P2
(45) Date of Patent: Feb. 13, 2007

(54) CRAPEMYRTLE PLANT NAMED 'GAMAD V'

(50) Latin Name: *Lagerstroemia L.*
Varietal Denomination: Gamad V

(75) Inventor: Michael A. Dirr, Bogart, GA (US)

(73) Assignee: University of Georgiea Research Foundation, Inc., Athens, GA (US)

( * ) Notice: Subject to any disclaimer, the term of this patent is extended or adjusted under 35 U.S.C. 154(b) by 0 days.

(21) Appl. No.: 11/205,282

(22) Filed: Aug. 16, 2005

(51) Int. Cl.
*A01H 5/00* (2006.01)

(52) U.S. Cl. ..... Plt./252
(58) Field of Classification Search ..... Plt./252
See application file for complete search history.

(56) References Cited

U.S. PATENT DOCUMENTS

PP7,966 P * 9/1992 Katsuo ..... Plt./252

OTHER PUBLICATIONS http://ecolage.safeshopper.com/247/2557.htm?987.*

* cited by examiner

*Primary Examiner*—Wendy Haas
(74) *Attorney, Agent, or Firm*—Greenlee Winner and Sullivan PC

(57) ABSTRACT

A new and distinct cultivar of crapemyrtle, *Lagerstroemia L.*, which is characterized by compact, mounded, true genetic dwarf growth habit; early flowering (beginning in late June to July in Athens, Ga.); extremely floriferous with bubble gum pink flowers, high mildew resistance.

2 Drawing Sheets

Botanical classification: *Lagerstroemia L.*
Varietal denomination: 'Gamad V'.

BACKGROUND OF THE INVENTION

The present invention relates to a new and distinct cultivar of the ornamental flowering shrub *Lagerstroemia L.*, commonly known as crapemyrtle, and hereafter referred to by the varietal denomination 'Gamad V'.

The new crapemyrtle was selected from approximately 1,000 seedlings grown from seed collected in 1997 from a collection of dwarf crapemyrtles growing in Athens, Ga. The specific parents of these seedlings are unknown. 'Gamad V' was selected in the summer of 1998 by the inventor as a single compact plant, with good mildew resistance and with abundant pink flowers at Dearing, Ga.

SUMMARY OF THE INVENTION

Plants of the cultivar 'Gamad V' have not been observed under all possible environmental conditions. The phenotype may vary somewhat with variations in environment such as light-intensity, temperature and cultural conditions, however, without any variance in genotype.

The following characteristics have been consistently observed and, to the best knowledge of the inventor, their combination form the unique characteristics of 'Gamad V' as a new and distinct cultivar.

1. Compact, mounded true genetic dwarf habit.
2. High leaf mildew resistance.
3. Early flowering begins in late June to July.
4. Abundant pink flowers that literally shroud the foliage.

Plants of the new crapemyrtle have been compared to the only pink flowering dwarf crapemyrtle known to the inventor, 'Chickasaw' (unpatented).

Comparative evaluations in containers and in the ground at Athens, Ga. showed that 'Gamad V' differed from 'Chickasaw' in the following characteristics:

1. Plants of 'Gamad V' produced more abundant flowers than 'Chickasaw'.
2. The flowers of 'Gamad V' open fully, compared to flowers of 'Chickasaw' which do not fully open.
3. Plants of 'Gamad V' flowered earlier than 'Chickasaw'.
4. Plant of 'Gamad V' maintained a dwarf habit and did not have the irregular habit of 'Chickasaw' which often produces reversion shoots.
5. Plant of 'Gamad V' were more resistant to mildew than 'Chickasaw'.

Asexual reproduction via tissue culture micropropagation and by traditional vegetative cuttings since the summer of 1998 has shown that the unique characteristics of this new crapemyrtle are stable and reproduced true-to-type in successive generations.

BRIEF DESCRIPTION OF THE PHOTOGRAPHS

The accompanying colored photographs illustrate the unique characteristics of the new cultivar, showing the colors as true as it is reasonably possible to obtain in colored reproductions of this type. Colors in the photograph may differ from the color values listed in the detailed botanical description which accurately describe the colors of the new crapemyrtle.

Figure 1:
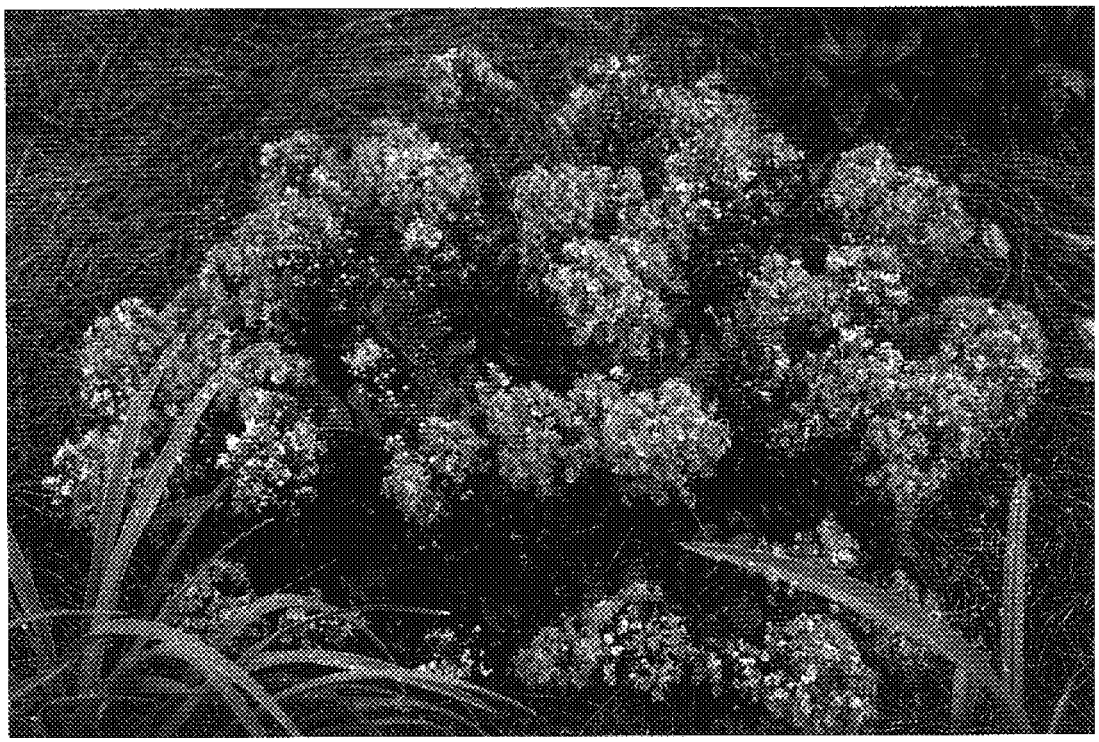

FIG. 1. A one-year-old plant growing in the ground at Chapel Hill, N.C. The picture was taken in July 2004.

Figure 2:
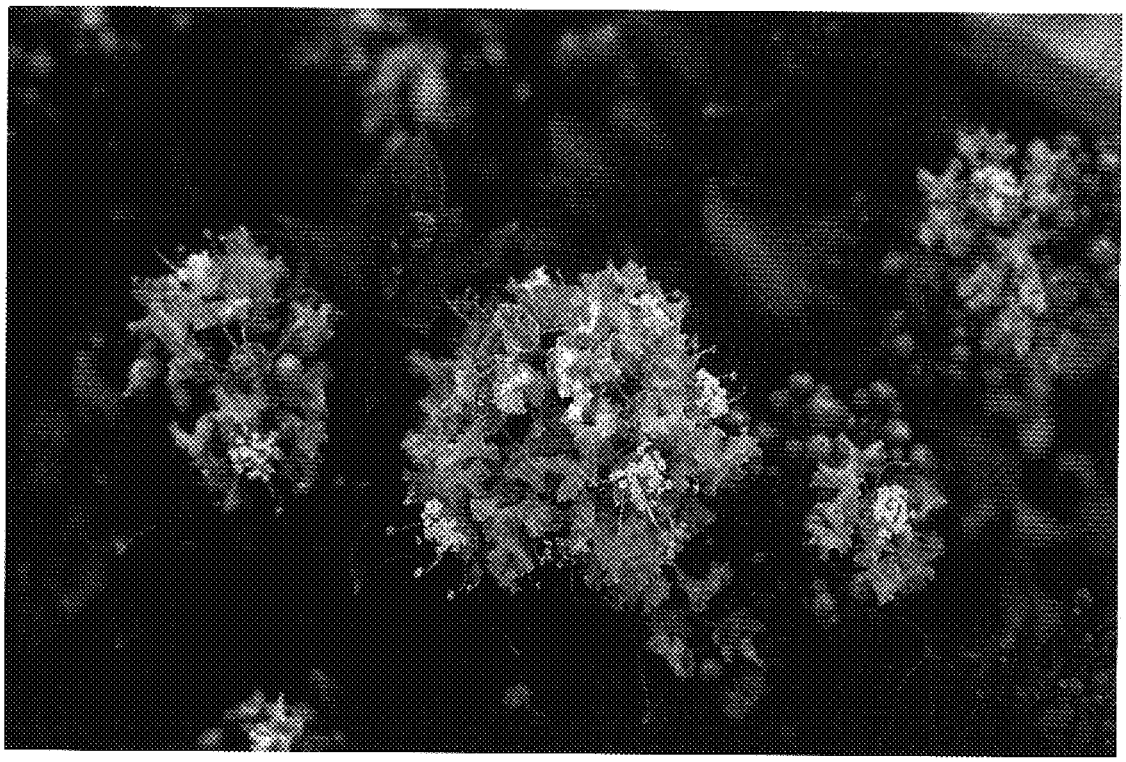

FIG. 2. Flowers of the one-year-old plant, showing the multiple long and short stamens.

DETAILED BOTANICAL DESCRIPTION

The botanical description of 'Gamad V' is based on three-year-old plants, growing in 22 liter containers in an outside nursery research facility in Athens, Ga. (USDA Zone 7b) under conditions which closely approximate commercial production. Measurements are based on the average of 10 to 20 samples, and were taken throughout the main growth period, from March through September in Athens, Ga. Colors are based on The Royal Horticultural Society Chart, 1995 edition.

The plant has a compact, broad-rounded growth habit with medium texture of branching, attaining an average height of 61 cm and width of 101 cm.

First year stems are square with wings, 1.0 mm across, with average internode length of 7.7 mm. They are Greyed-Orange 164A in color, without exfoliation.

Second year stems are oval, without wings, and are 1.5 mm across. The color is Greyed-Orange 177B, exfoliating to Greyed-White 156A.

Mature stems are up to 1.5 cm in diameter, exfoliating and Greyed-White 156A in color.

The vegetative buds are opposite to sub-opposite on all years growth, imbricate and conical in shape, 1 mm in length and 1 mm in width, with no pubescence, and the bud scales are Grey-Orange 176A in color.

The mature leaf, measured in the middle section of first year stems, averages 42 mm in length and 21 mm in width.

The leaf is elliptical, with an acuminate apex, cuneate base and entire, undulating margin. The emerging leaf (April in Athens, Ga.) is Yellow-Green N 146A on upper and Yellow-Green 146B on the lower surface, and both surfaces have a margin of Greyed-Purple 183A. In summer (August), the upper surface is Yellow-Green 147A and the lower surface is Green 137C.

The leaves are arranged opposite to sub-opposite on the stem, 0.5 mm thick with very shiny upper and semi-shiny lower surfaces. The venation is pinnate and the vein color is Green 138C. The petiole is 2 mm in length and 2 mm in diameter, with fine pubescence and Yellow-Green 146B in color.

The flower buds are 5 mm in length and 5 mm in width, rounded in shape with no pubescence, and are Yellow-Green 144C maturing to Greyed-Red 181B in color.

The flowering period is from late June to September in Athens, Ga.

The inflorescence averages 12.7 cm in length and 9.7 cm in width, and a plant in a 11.8 liter container carries 30 to 40 inflorescences. The color at emergence is Purple 76A, Red-Purple 73B in full bloom, fading to Violet 84B. There are 25 to 35 flowers per inflorescence. The individual flower averages 29.5 mm by 29.5 mm.

There are 6 petals per flower which average 10 mm in length and 9 mm in width, are fan-shaped with a ruffled, rounded apex, sagittate base and ruffled margin. There is no pubescence. The petal stalk averages 4.6 mm in length and is Red-Purple 73D at peak bloom, fading to Purple N 78D.

The calyx is Yellow-Green 145C inside and Greyed-Orange 173B to Yellow-Green 145A outside.

The pedicels are 7 mm long, with no pubescence and are Greyed-Orange 177A in color.

There is an average of 35 stamens in a cluster, with about 30 short stamens in the center and 5 to 6 longer stamens around the outside. The anthers are Yellow 13 A aging to Yellow-Orange 21B in color. The filaments average 8.6 mm in length and are Yellow 4D in color.

The style is 1.3 cm in length, Greyed-Yellow 160 B in color. The stigma is Yellow-Green 148A in color. There is a single ovary, 2 mm in diameter, with no pubescence, and Greyed-Yellow 160A in color.

The mature fruit is a six-valved dehiscent, broad ellipsoidal capsule, measuring 6 to 8 mm in length and 6 to 8 mm in width, prior to dehiscence. The color is Brown 200A. There are multiple seeds per capsule, averaging 6 mm long, and 3 mm wide, with a membraneous wing. The color of the seed is Brown 200A, and the wing is Grey-Brown 199D.

I claim:

1. A new and distinct cultivar of crapemyrtle plant named 'Gamad V', substantially as illustrated and described.

* * * * *